US010238543B2

(12) United States Patent
Farley (10) Patent No.: US 10,238,543 B2
(45) Date of Patent: Mar. 26, 2019

(54) VITRECTOMY PROBE WITH AN OPTICAL FIBER SCANNER (71) Applicant: Novartis AG, Basel (CH)

(72) Inventor: Mark Farley, Laguna Hills, TX (US)

(73) Assignee: Novartis AG, Basel (CH)

(*) Notice: Subject to any disclaimer, the term of this patent is extended or adjusted under 35 U.S.C. 154(b) by 139 days.

(21) Appl. No.: 14/526,685

(22) Filed: Oct. 29, 2014

(65) Prior Publication Data
US 2016/0120699 A1 May 5, 2016

(51) Int. Cl.
A61F 9/008 (2006.01)
A61F 9/007 (2006.01)

(52) U.S. Cl.
CPC ........ A61F 9/00825 (2013.01); A61F 9/0084 (2013.01); A61F 9/00736 (2013.01); A61F 2009/00874 (2013.01)

(58) Field of Classification Search
None
See application file for complete search history.

(56) References Cited

U.S. PATENT DOCUMENTS

| 3,982,541 A | 9/1976 | L'Esperance, Jr. |
| 3,990,453 A | 11/1976 | Douvas et al. |
| 4,122,853 A | 10/1978 | Smith |
| 4,168,707 A | 9/1979 | Douvas et al. |
| 4,200,106 A | 4/1980 | Douvas et al. |
| 4,583,539 A * | 4/1986 | Karlin ............... A61B 18/20 219/121.74 |
| 4,694,828 A | 9/1987 | Eichenbaum |
| 4,865,029 A * | 9/1989 | Pankratov ............ A61B 18/20 606/4 |
| 5,425,730 A | 6/1995 | Luloh |
| 5,505,693 A | 4/1996 | Mackool |
| 5,688,264 A | 11/1997 | Ren et al. |
| 5,957,914 A | 9/1999 | Cook et al. |
| 6,027,493 A * | 2/2000 | Donitzky ............ A61F 9/00736 606/10 |
| 6,263,879 B1 * | 7/2001 | Lin ....................... A61F 9/008 128/898 |

(Continued)

FOREIGN PATENT DOCUMENTS

| DE | 4038773 A1 | 6/1992 |
| DE | 19720660 A1 | 11/1998 |

(Continued)

OTHER PUBLICATIONS

International Searching Authority, International Search Report, PCT/US2015/053151, dated Dec. 23, 2015, 7 pages.

(Continued)

Primary Examiner — Michael Kahelin
Assistant Examiner — Qingjun Kong (57) ABSTRACT A vitrectomy probe for treating an eye of a patient, the probe including a body arranged for grasping by a surgeon, and a photodisruption element extending from the body. The photodisruption element includes a needle having a main lumen extending from the body, the needle comprising a port at an end, a fiber cannula within the main lumen, the fiber cannula having a fiber lumen, and an optical fiber within the fiber lumen, the optical fiber being mechanically agitatable within the fiber lumen.

20 Claims, 6 Drawing Sheets (56) References Cited

U.S. PATENT DOCUMENTS

| | | | |
|---|---|---|---|
| 7,285,107 B1* | 10/2007 | Charles | A61M 1/0045 604/28 |
| 8,641,701 B2 | 2/2014 | Hangai et al. | |
| 2004/0133190 A1 | 7/2004 | Hobart et al. | |
| 2005/0154379 A1 | 7/2005 | McGowan, Sr. et al. | |
| 2006/0100613 A1* | 5/2006 | McArdle | A61F 9/008 606/4 |
| 2006/0161145 A1 | 7/2006 | Lin et al. | |
| 2007/0265602 A1* | 11/2007 | Mordaunt | A61F 9/008 606/4 |
| 2008/0208233 A1 | 8/2008 | Barnes et al. | |
| 2012/0310042 A1* | 12/2012 | Joos | A61B 18/20 600/108 |
| 2013/0090635 A1 | 4/2013 | Mansour | |
| 2013/0144278 A1 | 6/2013 | Papac et al. | |
| 2013/0150839 A1 | 6/2013 | Smith et al. | |
| 2013/0158392 A1 | 6/2013 | Papac et al. | |
| 2013/0158393 A1 | 6/2013 | Papac et al. | |
| 2014/0128853 A1* | 5/2014 | Angeley | A61F 9/00827 606/4 |
| 2016/0113722 A1 | 4/2016 | Heeren | |

FOREIGN PATENT DOCUMENTS

| | | | |
|---|---|---|---|
| EP | 919210 A1 | 6/1999 | |
| EP | 2306919 B1 | 4/2011 | |
| GB | 1349881 A | 4/1974 | |
| JP | 11318968 A | 11/1999 | |
| JP | 2004261313 A | 9/2004 | |
| WO | 9633538 A1 | 10/1996 | |
| WO | 9944554 A2 | 9/1999 | |
| WO | 2007/000388 A1 | 1/2007 | |
| WO | 2008108425 A1 | 9/2008 | |
| WO | 2012/162493 A2 | 11/2012 | |
| WO | 2012152496 A1 | 11/2012 | |
| WO | WO 2014145465 A2 * | 9/2014 | A61F 9/00821 |
| WO | 2016/069179 A1 | 5/2016 | |

OTHER PUBLICATIONS

International Searching Authority, Written Opinion of the International Searching Authority, PCT/US2015/053151, dated Dec. 23, 2015, 9 pages.

Douvas, Nicholas G., Microsurgical Roto-Extractor Instrument for Vitrectomy, New Research on the Aetiology and Surgery of Retinal Detachment Mod. Probl. Ophthal., 1975, pp. 253-260, vol. 15, Karger, Basel.

Calhoun, et al, The Roto-Extractor in Pediatric Ophthalmology, Tr. Am. Ophth. Soc., pp. 292-305, 1975, vol. LXXIII.

Museum of Vision, Dedicated to Preserving Ophthalmic History, Museum of Vision: Collection Objects, The Foundation of the American Academy of Ophthalmology, http://www.museumofvision.org/collection/artifacts?accession=2004.004.00001, instrument dated 1970, pp. 1-4.

Meadow, Norman B., Vitreous history in the making, Ophthalmology Times, Jul. 15, 2013, pp. 1-3.

* cited by examiner

VITRECTOMY PROBE WITH AN OPTICAL FIBER SCANNER

FIELD OF THE INVENTION

The present disclosure relates to apparatuses and methods for ophthalmic medical procedures, and more particularly, to apparatuses and methods including cutting and/or removal of the vitreous humor.

BACKGROUND

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibrils that are often attached to the retina. Therefore, cutting and removal of the vitreous must be done with great care to avoid traction on the retina, the separation of the retina from the choroid, a retinal tear, or, in the worst case, cutting and removal of the retina itself. Delicate operations such as mobile tissue management (e.g., cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Standard vitrectomy probes typically include a hollow needle with a port on the end to pull in fibrils forming the vitreous humor. An inner member, placed within the hollow needle, moves back and forth to open and close the port. This operates to cut any fibrils that enter the port while it is open. The rapid back and forth movement of the inner member can cause undesired vibrations within the vitrectomy probe. There is a need for continued improvement in the use and operability of vitrectomy probes. The probes discussed herein are arranged to address one or more of the deficiencies in the prior art.

SUMMARY

This disclosure relates generally to, and encompasses, apparatuses and methods for removing fluid from the eye, and more specifically to ophthalmic surgical systems and methods of using the systems to remove fluid from the eye.

According to one example, this disclosure relates to a vitrectomy probe for treating an eye of a patient. The probe includes a body arranged for grasping by a surgeon and a photodisruption element extending from the body. The photodisruption element includes a needle having a main lumen extending from the body, with the needle comprising a port at an end. The photodisruption element also includes a fiber cannula within the main lumen, the fiber cannula having a fiber lumen. The photodisruption element also includes an optical fiber within the fiber lumen, the optical fiber being mechanically agitatable within the fiber lumen.

According to one example, an ophthalmic surgical system includes a probe having a body arranged for grasping by a surgeon and a photodisruption element extending from the body. The photodisruption element includes a needle having a main lumen comprising a port at an end, a fiber cannula having a fiber lumen, and an optical fiber within the fiber lumen. The system also includes an agitation mechanism to agitate the optical fiber within the fiber lumen such that a beam extending from the optical fiber scans the port.

According to one example, a method for operating a vitrectomy probe includes projecting a laser beam from a surface of an optical fiber, with the laser beam being directed across a port within a needle of the vitrectomy probe. The optical fiber is housed within a fiber cannula that is within the needle, the fiber cannula having a fiber lumen. The method further includes mechanically agitating the optical fiber within the fiber lumen such that the laser beam scans across the port.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to apparatuses, systems, and methods for removing ocular tissue and/or fluid from the eye. The various figures show embodiments of exemplary ophthalmic surgical probes and methods of using the devices to remove ocular tissue and/or fluid from a patient's eye. Embodiments described herein incorporate a photodisruption element of a vitrectomy probe that may operate to sever vitreous fibrils during a vitrectomy procedure. One of ordinary skill in the art, however, would understand that similar embodiments could be used to remove tissue and/or fluid from other locations in the body without departing from the general intent or teachings of the present disclosure.

Figure 1:
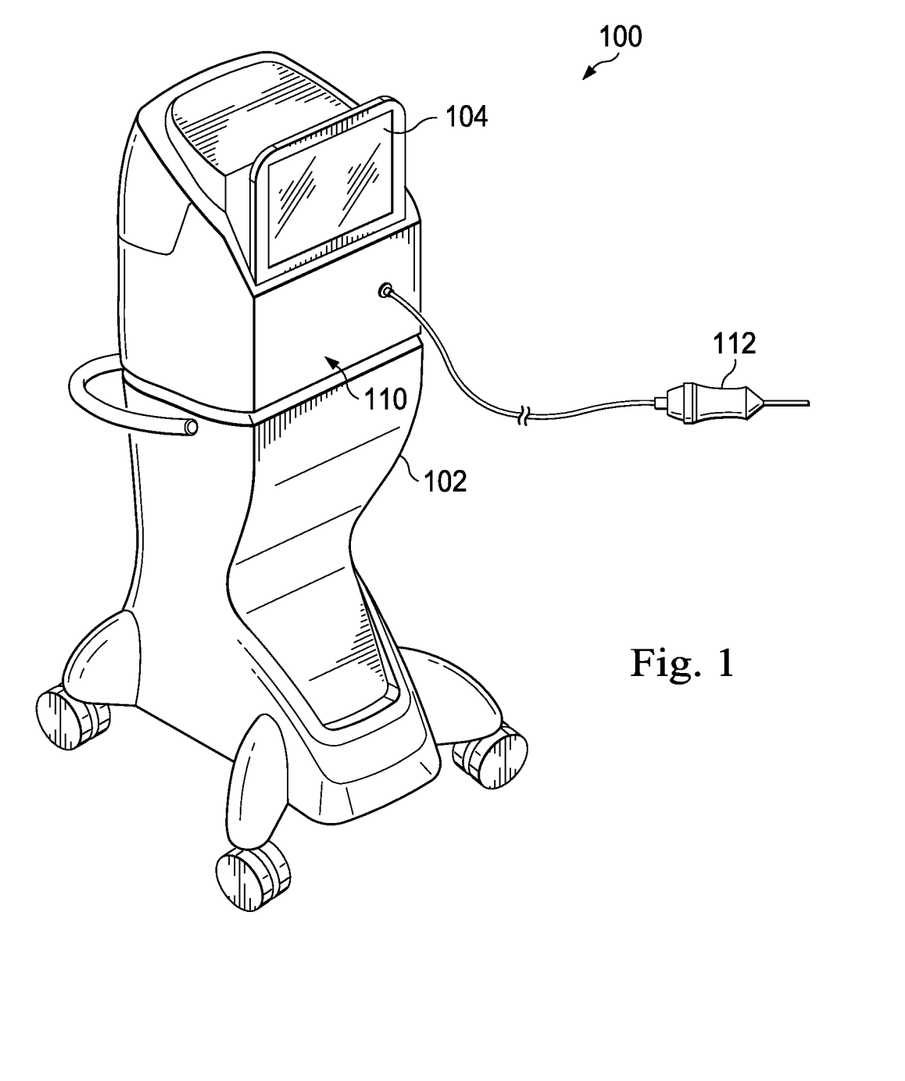
FIG. 1 is a diagram showing an illustrative vitrectomy probe system according to one example incorporating the principles described herein.

FIG. 1 is a diagram showing an illustrative vitrectomy surgical system 100. According to the present example, the vitrectomy surgical system 100 includes a base housing 102 and an associated display screen 104 showing data relating to system operation and performance during a vitrectomy surgical procedure. In this exemplary embodiment, the vitrectomy surgical system 100 includes a mobile console that may be used by a health care provider to perform a vitrectomy surgical procedure. The vitrectomy surgical system 100 includes a vitrectomy probe 112 that is configured to be used during an ophthalmic surgical procedure, such as, for example, a vitrectomy surgical procedure. The base housing 102 may be configured to process, receive, and store data and provide signals to the vitrectomy probe and/or the display 104.

Figure 2:
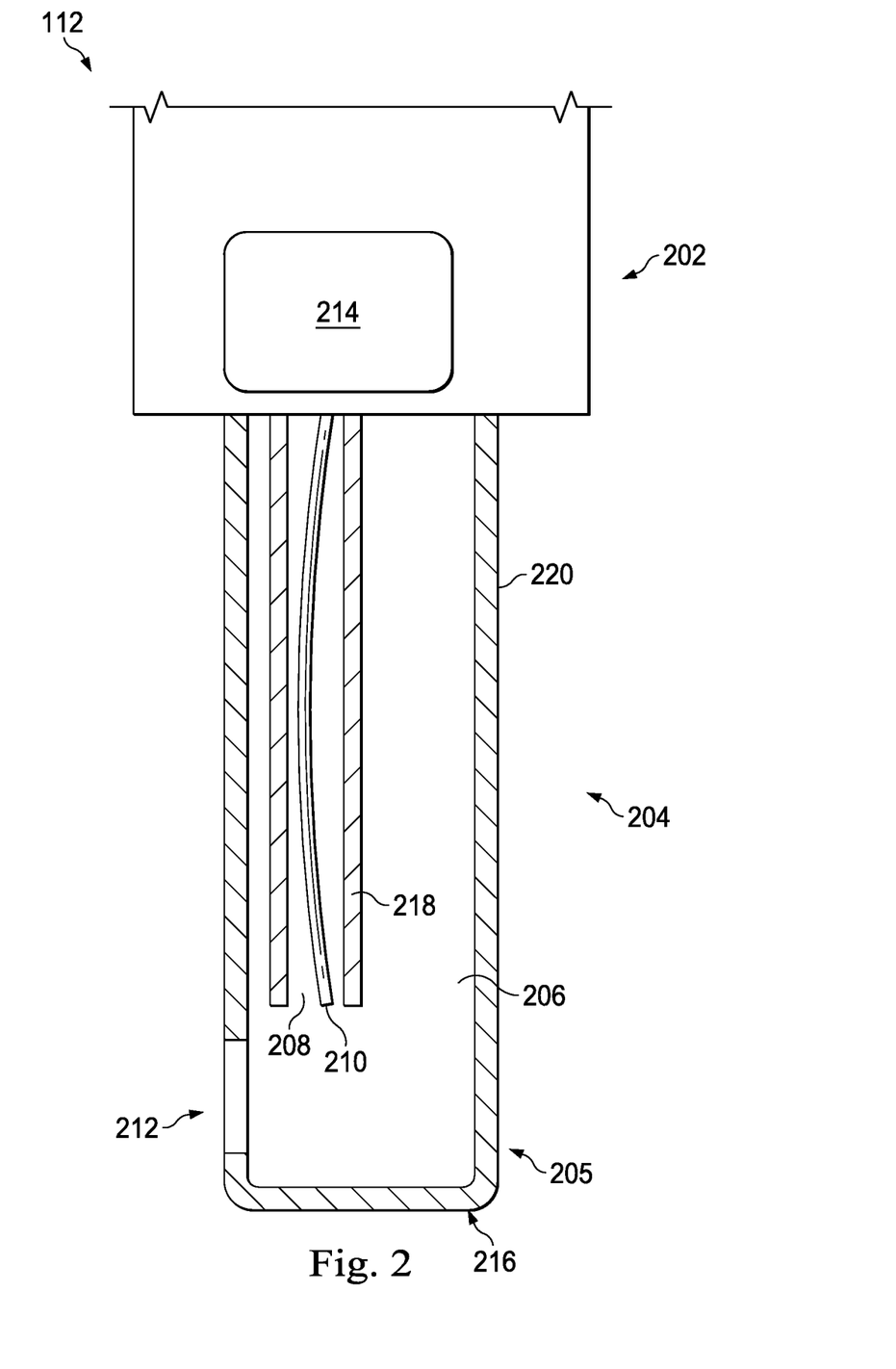
FIG. 2 is a diagram showing an illustrative longitudinal cross-sectional view of a portion of vitrectomy probe with a photodisruption element according to one example incorporating the principles described herein.

FIG. 2 is a stylized diagram showing a portion of the illustrative vitrectomy probe 112. According to the present example, the vitrectomy probe 112 includes a body 202 and a photodisruption element 204 supported by and extending therefrom. The photodisruption element 204 includes a main lumen 206 having a port 212 at the end. The photodisruption element 204 also includes a fiber lumen 208 with an optical fiber 210 therein.

The body 202 forms a handle portion that may be grasped and manipulated by a surgeon when performing a surgical procedure, such as a vitrectomy. In some embodiments, the exterior portion of the body 202 is ergonomically designed for comfortable grasping by the surgeon. The body 202 may be made from a variety of materials commonly used to form such tools. For example, the body 202 may be made of, for example, a lightweight aluminum, a polymer, or other material. Depending on the embodiment, it may be sterilized and used in more than surgical procedure, or it may be a single-use device. The inner portion of the body 202 is designed to house an agitation mechanism 214. The agitation mechanism is a motor or driver and will be described in greater detail below. The inner portion of the body 202 is also designed to support the photodisruption element 204 and other features or elements of the probe 112.

The photodisruption element 204 is a portion of the probe 112 that interfaces with the patient. It is designed to penetrate a globe of an eye and may be used to remove vitreous or perform other functions or tasks. The photodisruption element 204 includes a needle 216, a fiber cannula 218, and an optical fiber 210. The needle 216 includes a distal tip 205, a main lumen 206, and a cylindrical body portion 220. The cylindrical body portion 220 includes a port 212 near the distal tip 205. In one example, the main lumen 206 has a substantially circular cross-section. Other embodiments have other cross-sectional shapes, including oval, rectangular, among others. Yet other cross-sectional shapes are also contemplated. The port 212, which is at the distal tip 205 of the needle 216, is sized and shaped to allow vitreous fibrils to enter the main lumen 206. As will be described in further detail below, a laser beam projecting from the optical fiber 210 will sever the vitreous fibrils that enter the port 212.

The fiber cannula 218 is disposed within the main lumen 206 of the needle 216. It includes a fiber lumen 208 and is designed to house the optical fiber 210. The fiber cannula 218 may be rigidly fixed in place and may be secured in place along an interior of the needle 216, or may float within the main lumen 206. In some embodiments, the fiber cannula 218 is formed within a wall of the needle 216. In one example, the outer surface of the fiber cannula 218 is secured to the inner surface of the needle 216. The interior of the fiber cannula 218 has a diameter that is substantially larger than the outer diameter of the optical fiber 210 such that the optical fiber 210 is able to displace within the fiber lumen 208. The outer diameter of the fiber cannula 218 is sized and shaped to fit within the main lumen 206 while leaving enough room within the interior of the main lumen 206 for other purposes, such as the aspiration of emulsified or photodisrupted tissue, including vitreous fibrils.

The optical fiber 210 is designed to act as an optical waveguide and propagate a laser beam. The characteristics of the laser beam propagated through the optical fiber 210 are such that the laser beam causes photodisruption of vitreous fibrils within the path of the laser beam. In some examples, the laser beam may be produced by an Yttrium Aluminum Garnet (YAG) laser incorporated in the body 202 of the probe 112, in the base housing 102, or at another location about the surgical system 100. The laser beam may have an energy output within a range of about 1 micro-joule (µJ) to 10 milli-joules (mJ). The laser may be a pulsed laser having a pulse width within a range of about 10-1000 femtoseconds (fs). The laser may have a pulse rate within a range of about 10-500 kilohertz (kHz). These ranges can effectively provide photodisruption, which is the mechanical effect of light on tissue to disrupt or breakdown the tissue by laser-produced rapid ionization of molecules. Other ranges for characteristics of the laser beam that can provide photodisruption are contemplated as well.

The optical fiber 210 is positioned such that a laser beam projecting from the optical fiber 210 will be projected across the port 212 and has power sufficient to sever vitreous fibrils. Thus, the laser beam can sever vitreous fibrils that enter the port 212. In the embodiments disclosed herein, the width of the laser beam may be substantially smaller than the width of the port 212. For example, the port 212 may have a diameter or width of approximately 300 microns. The laser beam itself may have a diameter of approximately 10 to 25 microns. According to principles described herein, the optical fiber 210 is set into motion by the agitation mechanism 214 such that movement of the optical fiber 210 causes a laser beam being projected from the optical fiber 210 to scan across the port 212.

The agitation mechanism 214 is configured to mechanically move the optical fiber 210 within the fiber lumen 208. Thus, the size of the fiber lumen 208 and size of the optical fiber 210 are such that there is room for the optical fiber 210 to physically move within the fiber lumen 208. Specifically, the diameter of the fiber lumen is larger than the outer diameter of the fiber lumen. In some embodiments, the agitation mechanism 214 is a motor or driver that displaces the optical fiber 210. As described above, the optical fiber 210 and fiber lumen 208 are sized such that the optical fiber 210 has room to move within the fiber lumen 208. The agitation mechanism 214 may move the optical fiber 210 in a variety of different ways at varying frequencies. For example, the agitation mechanism 214 may move the optical fiber 210 at a frequency within a range of about 10 hertz (Hz) to 10 kHz. This rapid movement of the optical fiber 210 causes the laser beam being projected from the optical fiber 210 to move across the port 212 fast enough so that vitreous fibrils entering the port 212 will be within the path of the laser beam. Depending upon the embodiment, the agitation mechanism 214 displaces the optical fiber 210 in a back and forth or side-to-side motion, a circular rotation, a random path, or other displacement pathway. The laser beam can then sever the vitreous fibrils through a photodisruption process.

Figure 3A:
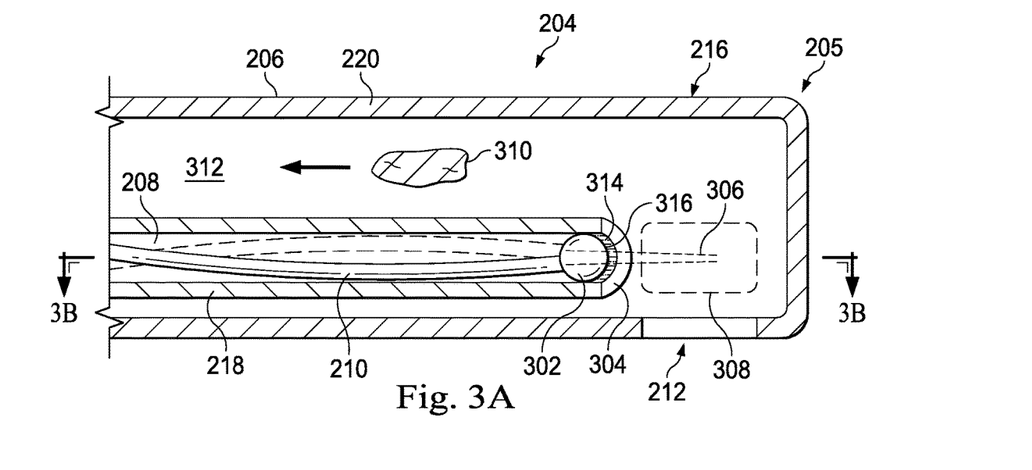
FIGS. 3A and 3B are diagrams showing illustrative longitudinal cross-sectional views of a photodisruption element of a vitrectomy probe with an optical fiber scanner according to one example incorporating the principles described herein.
Figure 3B:
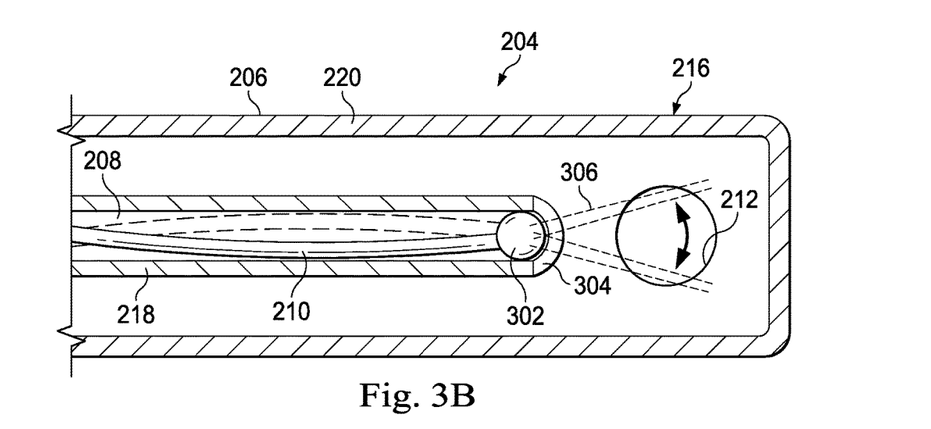

FIGS. 3A and 3B are diagrams showing illustrative longitudinal cross-sectional views of a photodisruption element 204 of a vitrectomy probe 112 with an optical fiber scanner. FIG. 3A illustrates a view along a cross-section that is perpendicular and through the port 212. FIG. 3B illustrates a view taken along lines 3B-3B in FIG. 3A, showing a cross-section that is parallel to the port 212.

In the example of FIG. 3A, the tip of the optical fiber 210 includes a rounded tip functioning as a lens of the optical fiber. The tip will thus be referred to as a lensed tip 302. The lensed tip 302 may be a solid, round end of the optical fiber 210. The lensed tip 302 may have a diameter that is larger than the diameter of the optical fiber 210. The lensed tip 302 may be made of the same material as the optical fiber 210 and thus be transparent. The lensed tip 302 may function independently, or in conjunction with a lens 304, to provide refractive focusing power. This can provide a means to concentrate the energy of the projected laser beam by reducing the divergence of the beam, collimating the beam, or converging the beam to a spot smaller than the optical fiber diameter.

In some examples, the lensed tip 302 may also function as a bearing 302 in conjunction with a lens 304. The lensed tip or bearing 302 is sized and shape to fit within a lens 304 secured to the distal end of the fiber lumen 208. The lens 304 may be made of a transparent material such as glass or plastic. The lens 304 has a concave inner surface that receives the bearing 302. The outer surface of the lens 304 has a convex shape. The curvature of both the outer surface and the inner surface is selected to affect the laser beam 306 as desired. For example, the curvature of both surfaces of the lens 304 can cause the laser beam to be collimated, convergent, or divergent. In some examples there may be a lubricant 314 between the bearing 302 and the lens 304. The lubricant 314 may be a transparent fluid that has a refractive index that matches the refractive index of the material that forms the lens 304. This reduces the amount of reflection of the laser beam 306 being projected from the optical fiber 210. In some embodiments, a different kind of lubricant may be used. In some examples, no lubricant is used between the bearing 302 and the lens 304.

The agitation mechanism (e.g. 214, FIG. 2) can cause movement of the optical fiber 210 such that the bearing 302 rotates or spins within the lens 304 as the optical fiber 210 moves within the fiber lumen 208. As the bearing 302 rotates with respect to the lens 304, the distal end 316 of the optical fiber 210, through which a laser beam 306 is emitted, moves such that the laser beam 306 being projected from the distal end 316 of the optical fiber 210 scans across the port 212.

The optical fiber 210 may move in a variety of ways. For example, the optical fiber 210 may move in an elliptical or circular motion around the inner diameter of the fiber lumen 208. In some examples, the optical fiber 210 may move back and forth along a linear path across the fiber lumen 208. In some cases, the optical fiber 210 may move at random throughout the fiber lumen 208. More detail on the type of movement caused by the agitation mechanism will be provided below.

During operation of the vitrectomy probe 112, the surgeon moves the tip of the vitrectomy probe 112 such that vitreous fibrils enter into the port 212. As the vitreous fibrils enter the port 212 and pass into the photodisruption region 308, they will be severed as the scanning laser beam 306 moves past them.

In some examples, the vitrectomy probe 112 includes an aspiration lumen 312 for aspirating the severed vitreous tissue 310 and other vitreous fluids. The aspiration lumen 312 may be in connection with a suction mechanism (not shown) that provides a vacuum force to extract the severed tissue 310 and other fluids. In some embodiments, the suction mechanism is located on the console (e.g., 110, FIG. 1) and is in communication with the aspiration lumen 312 of the vitrectomy probe 112. In some examples, the main lumen 206 acts as part of the aspiration lumen as illustrated. In some examples, however, a separate and independent cannula with an aspiration lumen is positioned within the main lumen 206. Such an aspiration lumen is in connection with the port 212 so that severed tissue 310 will appropriately pass into the aspiration lumen.

FIG. 3B illustrates a cross-sectional view of the photodisruption element 204 taken along lines 3B-3B in FIG. 3A. Thus, it can be seen that the laser beam 306 scans across the circular port 212 as indicated by the double sided arrows. While the port 212 is illustrated as circular, it is understood that the port 212 may have other shapes, including elliptical and rectangular, for example.

Various repetition rates, focused spot diameters, spot densities, scanned areas, and scan patterns can be used in accordance with principles described herein. For example, a 30 kHz laser pulse rate with a focused beam diameter of 3 microns applied at 100% density over a 500 micron diameter port could be used in accordance with an agitation technique that involves a 50 Hz oscillation in an elliptical pattern. In another example, a 200 kHz laser pulse rate with a focused beam diameter of 10 microns applied at 50% density over a 300 micron diameter circular area could be used in accordance with a 4500 Hz oscillation in an elliptical path.

In some examples, the laser beam 306 is configured such that it converges as it crosses the port 212. A converging laser beam has a diameter that decreases over a specific length. A converging laser beam focuses more energy into a smaller cross-sectional area, thus allowing for better photodisruption at the smaller area.

Figure 4A:
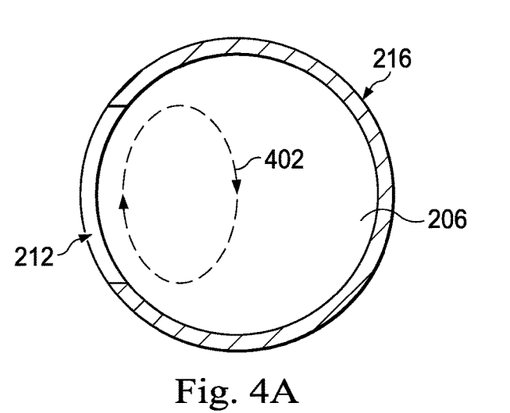
FIGS. 4A-4C are diagrams showing axial cross-sectional views of a path taken by a scanning laser beam according to one example of principles described herein.
Figure 4B:
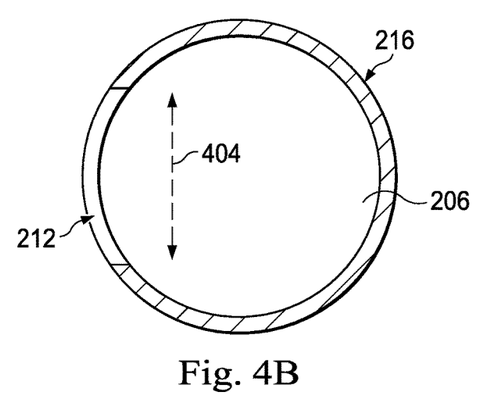
Figure 4C:
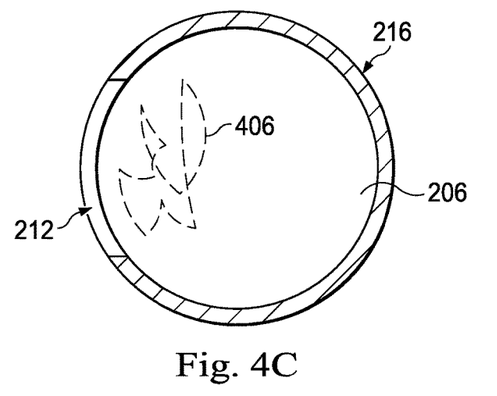

FIGS. 4A-4C are diagrams showing axial cross-sectional views of exemplary paths taken by a scanning laser beam. The cross-sectional view illustrates the main lumen 206 and the port 212 of the needle 216. FIG. 4A illustrates an elliptical path 402. In some examples, the agitation mechanism (e.g., 214, FIG. 2) is configured to cause the optical fiber (e.g., 210, FIG. 2) to move in an elliptical or circular motion resulting in a travel path of the laser beam corresponding to an elliptical shape as the beam travels across the port 212. In some examples, this may cause the bearing (e.g., 302, FIG. 3A) to rotate within the lens (e.g., 304, FIG. 3A) such that the laser beam (e.g., 306, FIG. 3A) emitted from the optical fiber makes the illustrated elliptical path. While the elliptical path 402 is shown as being clockwise, it is understood that the agitation mechanism can cause counter-clockwise motion as well.

FIG. 4B illustrates a linear path 404. In some examples, the agitation mechanism is configured to cause the optical fiber to move such that the laser beam moves back and forth in a linear pattern across the port 212 as illustrated in the linear path 404. The frequency at which the laser beam moves back and forth may be selected to effectively cause photodisruption of tissue that has passed through the port 212 into the main lumen 206.

FIG. 4C illustrates a random path 406. In some examples, the agitation mechanism is configured to randomly agitate the optical fiber such that the laser beam moves in a random path 406. The speed and manner in which the optical fiber is agitated to move in the random path 406 may be selected to effectively cause photodisruption of tissue that has passed through the port 212 into the main lumen 206.

Figure 5:
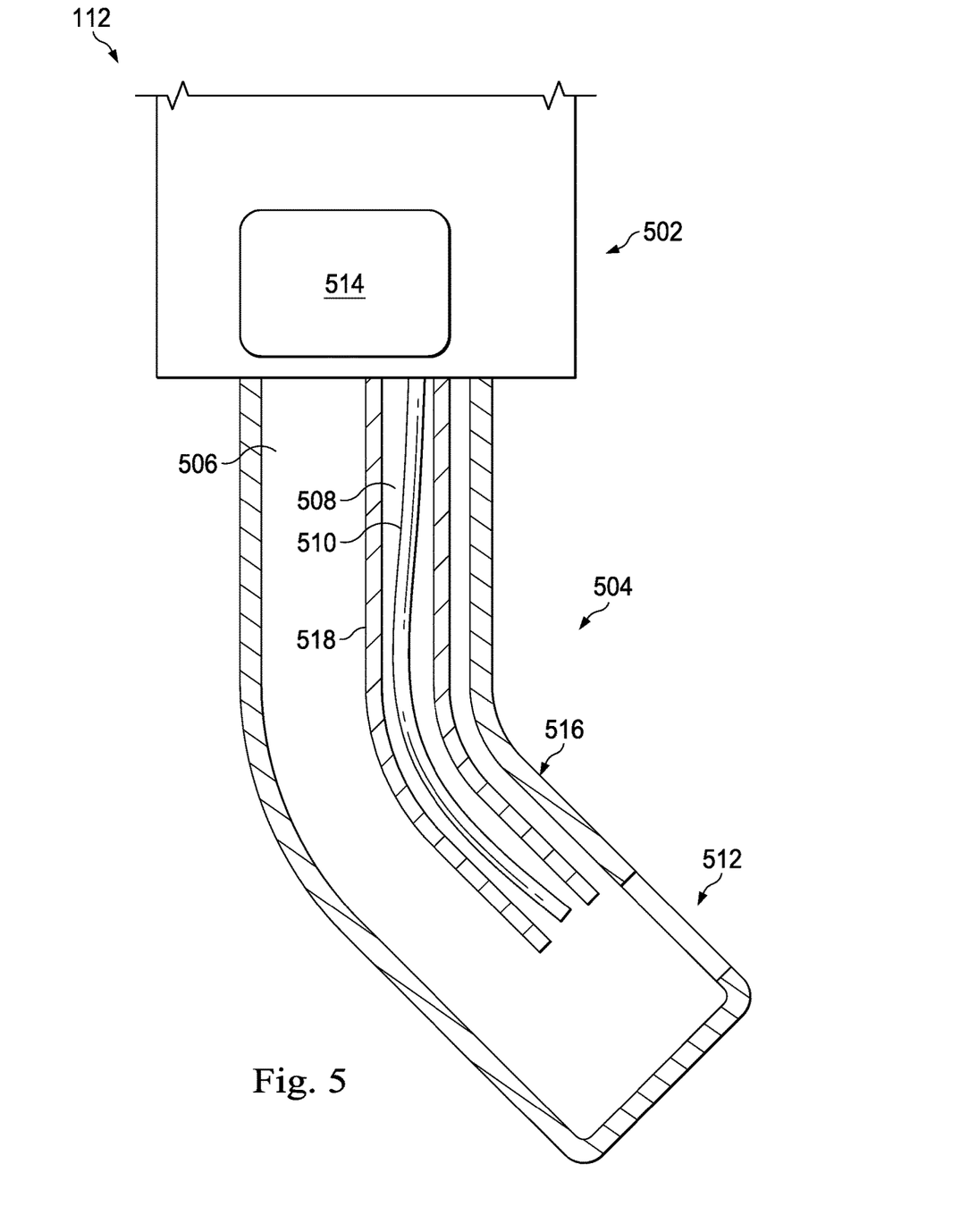
FIG. 5 is a diagram showing an illustrative vitrectomy probe with a curved photodisruption element according to one example of principles described herein.

FIG. 5 is a stylized diagram showing an illustrative vitrectomy probe 112 with a curved photodisruption element 504. As described above, conventional vitrectomy probes use a mechanical cutting element to sever vitreous fibrils that enter the port. The mechanical cutting element generally includes an inner member that moves axially across the port. This axial motion is not amenable to having a curved cutting element. But, using principles described herein, the photodisruption element 504 can be curved to allow for improved access to remove tractional attachments in the anterior vitreous base, and avoid contact with the crystalline lens. Better access allows for improved surgical outcomes.

According to the present example, the photodisruption element 504 includes a needle 516 with a main lumen 506 extending from a body 502. Here, the needle 516 is curved. In some examples, a curved needle has an arcing along at least a portion of the length of the needle 516. In some examples, the entire length of the needle 516 is arced. In some examples, a curved needle has one or more bends between straight sections. For example, as illustrated in FIG. 5, the curved needle 516 has a single bend between two straight sections.

Additionally, a fiber cannula 518 with a fiber lumen 508 that houses the optical fiber 510 is curved in a manner similar to that of the needle 516. Because bending an optical fiber 510 does not prevent the propagation of light through the optical fiber 510, it is possible to have a curved photodisruption element 504 as illustrated. The descriptions herein of the body and the agitation mechanism, as well as other features also apply to the embodiment shown in FIG. 5 and will not be repeated here. The body 502 can be designed to support the curved photodisruption element 504. Additionally, the agitation mechanism 514 can be designed to agitate the curve optical fiber 510 such that a laser beam emitted from the tip of the optical fiber 510 causes photodisruption of tissue entering a port 512 in the needle 516.

Figure 6:
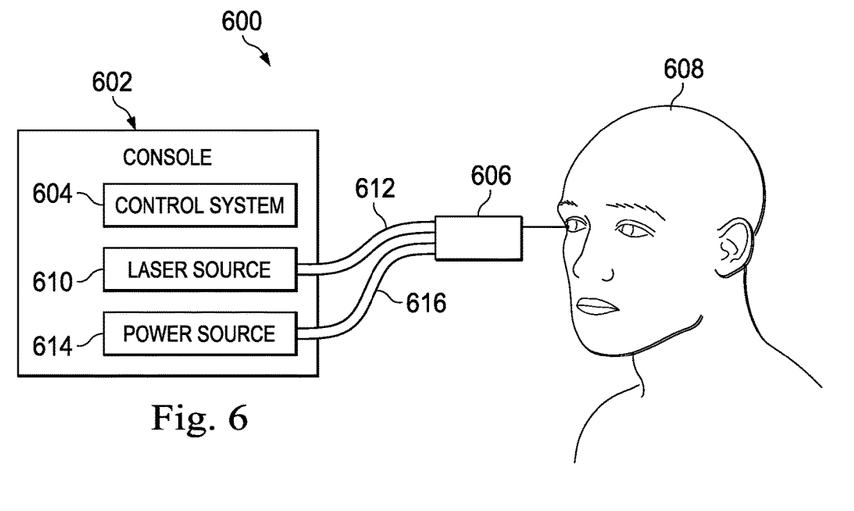
FIG. 6 is a diagram showing an ophthalmic surgical system with a photodisruption vitrectomy probe performing a surgical procedure on a patient according to one example incorporating the principles described herein.

FIG. 6 is a diagram showing an ophthalmic surgical system 600 with a photodisruption vitrectomy probe 606 performing a surgical procedure on a patient. According to the present example, the system 600 includes a console 602 with a control system 604, a laser source 610, and a power source 614. The console 602 is in communication with the probe 606, also referred to as a hand-piece 606. The hand-piece 606 may be the same probe 112 discussed above, or may be another probe used by an operator or surgeon to treat a condition of the eye. In this example, the distal portion is inserted into the eye of a patient 608.

Many of the details of these components are unchanged from those described with reference to other embodiments, and those descriptions will not be repeated here. The console 602 includes components that drive and work with the hand piece 606. Additional components and features of the console 602 would be apparent to one of ordinary skill in the art. The control system 604 within the console 602 provides the desired signals to the hand piece 606 to cause the waveguide or optical fiber to move with respect to the needle member and cut vitreous fibrils. The control system 604 may include a processor, a memory, and other hardware to control the console and the hand-piece 606.

The laser source 610 may provide a laser having the characteristics that allow for effective photodisruption. The laser source 610 may be in communication with the hand-piece 606 through an optical cable 612. The optical cable 612 includes a waveguide that is designed to effectively propagate the laser from the laser source 610 to the optical fiber (210, FIG. 2) within the hand-piece 606.

The power source 614 is used to power the agitation mechanism (210, FIG. 2) that agitates the optical fiber within the hand-piece 606. Various types of power sources may be used. In one example, if the agitation mechanism is electrically powered, then the power source 614 is an electrical power source such as a battery or voltage supply to provide the appropriate voltage. In such a case, the cable 616 is a power cable. In one example, if the agitation mechanism is pneumatically powered, then the power source 614 may be a compressed fluid supply. In such a case, the cable 616 would be a pneumatic tube connecting the compressed fluid supply to the hand-piece 606.

Other connections between the hand-piece 606 and the console 602 may be used as well. For example, the console may include a suction or aspiration mechanism that connects with an aspiration lumen on the hand-piece 606. While the optical cable 612 and the cable 616 are illustrated separately, in some cases, all connections between the console 602 and the hand-piece 606 may be fit within a single cable.

Figure 7:
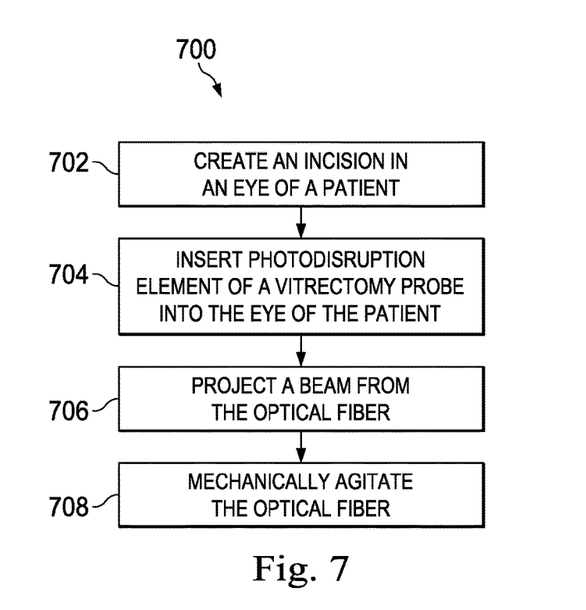
FIG. 7 is a flowchart showing an illustrative method for treating a patient with a vitrectomy probe having an optical fiber scanner according to one example incorporating the principles described herein.

FIG. 7 is a flowchart showing an illustrative method 700 for treating a patient with a photodisruption vitrectomy probe that has an optical fiber scanner. The optical fiber scanner includes the components used to cause a laser beam to move or scan across a port of the vitrectomy probe. According to the present example, the method 700 includes creating an incision in an eye of a patient at 702. At 704, the method 700 includes inserting a photodisruption element of a vitrectomy probe into the eye of the patient.

The photodisruption element includes a needle forming a main lumen. A port at the distal end of the needle permits vitreous fibrils to enter the main lumen. The photodisruption element also includes a fiber cannula forming a fiber lumen and includes an optical fiber housed therein. An agitation mechanism is arranged to agitate the optical fiber in the manner described herein.

According to the present example, the method 700 includes 706 for projecting a laser beam from the optical fiber. The characteristics of the laser beam are such that the beam effectively causes photodisruption of tissue in the path of the laser beam. In some examples, the laser beam may converge as it crosses the port. This focuses more energy into a smaller diameter and can allow for better photodisruption. Other embodiments have a diverging laser beam. Yet other embodiments have a substantially collimated laser beam.

The method further includes 708 for mechanically agitating the optical fiber. Agitating the optical fiber causes the tip of the optical fiber to move such that the laser beam being projected from the tip of the optical fiber scans across the port in the needle. Thus, even though the diameter of the laser beam is substantially smaller than the opening of the port, the laser beam can sever the tissues that enter the port because it moves back and forth across the port at a relatively rapid rate. With the optical fiber being mechanically agitated, the surgeon may complete a vitrectomy procedure by aspirating vitreous humor from the eye of the patient through the port in the needle. Vitreous that enters the port is severed and aspirated through the needle to the main housing, where the aspirated tissue will be collected in a disposal reservoir. When the procedure is complete, the needle is withdrawn from the patient's eye, and additional procedures, not involving the vitrectomy probe, may occur.

Use of principles described herein can provide several benefits to surgical operations involving a vitrectomy probe. For example, use of the laser beam rather than a mechanical cutting tool allows for a faster cut rate and can decrease retinal traction, which can cause tearing of the retina. The photodisruption vitrectomy probe can operate with less noise, vibration, and wear than conventional vitrectomy probes. Moreover, use of the photodisruption element allows for a curved probe tip, enabling better access and treatment in some instances than can be obtained with a straight needle.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A vitrectomy probe for treating an eye of a patient, the probe comprising:
    a body arranged for grasping by a surgeon; and
    a photodisruption element extending from the body, the photodisruption element including:
        a needle having a main lumen extending from the body, the needle comprising a port in a side wall of the needle, wherein the needle is closed at a distal-most end of the needle, wherein the port has a bottom and an opposing top, wherein the bottom of the port is adjacent the distal-most end of the needle and wherein a distance between the bottom and the top forms a height of the port, and the port has a first side and an opposing second side that are located between the top and bottom such that a distance between the first and second sides forms a width of the port;
        a fiber cannula within the main lumen, the fiber cannula having a fiber lumen and the fiber lumen having a longitudinal axis; and
        an optical fiber within the fiber lumen, the fiber lumen being positioned in the needle to direct a laser beam from the optical fiber across the port in the side wall of the needle;
        a motor coupled to the optical fiber, wherein the motor agitates the optical fiber within the fiber lumen to scan the laser beam in a direction transverse to the longitudinal axis, repeatedly across the port in the side wall between the first side and the second side, at a frequency within a range of 10 hertz (Hz) to 10 kHz, such that vitreous humor entering the port in the side wall is severed by the scanning laser beam.

2. The probe of claim 1, wherein the optical fiber comprises a rounded tip configured as a lens of the optical fiber.

3. The probe of claim 1, wherein the optical fiber comprises a bearing at a tip of the optical fiber.

4. The probe of claim 3, wherein the fiber lumen comprises a lens at a distal end of the fiber lumen, the lens shaped to fit the bearing such that agitation of the optical fiber causes the bearing to rotate within the lens.

5. The probe of claim 4, wherein a distal surface of the optical fiber is directed such that mechanical agitation of the optical fiber causes a beam being projected from the distal surface to scan the port.

6. The probe of claim 4, further comprising, wherein the main lumen is an aspiration lumen for extracting the vitreous humor that is severed by the laser beam projected from the optical fiber.

7. The probe of claim 4, wherein the optical fiber is configured to emit the laser beam that converges across the port.

8. The probe of claim 4, wherein the photodisruption element is curved.

9. An ophthalmic surgical system comprising:
    a probe comprising:
        a body arranged for grasping by a surgeon;
        a photodisruption element extending from the body, the photodisruption element including:
            a needle having a main lumen, the needle comprising a port in a side wall of the needle, wherein the needle is closed at a distal-most end of the needle, wherein the port has a bottom and an opposing top, wherein the bottom of the port is adjacent the distal-most end of the needle and wherein a distance between the bottom and the top forms a height of the port, and the port has a first side and an opposing second side that are located between the top and bottom such that a distance between the first and second sides forms a width of the port;
            a fiber cannula having a fiber lumen, wherein the fiber lumen has a longitudinal axis; and
            an optical fiber within the fiber lumen, the fiber lumen being positioned in the needle to project a laser beam from the optical fiber across the port in the side wall of the needle; and
        a motor coupled to the optical fiber to move the optical fiber in an elliptical motion within the fiber lumen such that the laser beam projecting from the optical fiber results in a travel path corresponding to an elliptical shape as the laser beam scans repeatedly, in a direction transverse to the longitudinal axis, at a frequency within a range of 10 hertz (Hz) to 10 kHz, across the port in the side wall, between the first side and the second side, of the needle such that vitreous humor entering the port in the side wall is severed by the scanning laser beam.

10. The system of claim 9, further comprising, a console connected to the probe through at least one cable,
    wherein the console comprises:
        a power source in connection with the motor; and
        a vacuum source in fluid connection with the probe; and
        a laser light source in optical connection with the optical fiber.

11. The system of claim 9, wherein the main lumen and the fiber lumen have a curved shape.

12. A method for operating a vitrectomy probe, the method comprising:
- projecting a laser beam from a surface of an optical fiber, the laser beam being projected across a port within a side wall of a needle of the vitrectomy probe having a closed distal end, the optical fiber being housed within a fiber cannula that is within the needle, the fiber cannula having a fiber lumen, wherein the fiber lumen has a longitudinal axis, and wherein the port has a bottom and an opposing top, wherein the bottom of the port is adjacent the closed distal end of the needle and wherein a distance between the bottom and the top forms a height of the port, and the port has a first side and an opposing second side that are located between the top and bottom such that a distance between the first and second sides forms a width of the port; and
- mechanically agitating the optical fiber within the fiber lumen such that the laser beam scans repeatedly, in a direction transverse to the longitudinal axis, at a frequency within a range of 10 hertz (Hz) to 10 kHz, across the port in the side wall of the needle between the first side and the second side, such that vitreous humor entering the port in the side wall is severed by the laser beam scanning the port.

13. The method of claim 12, wherein the laser beam is a pulsed laser beam.

14. The method of claim 13, wherein a pulse of the laser beam has a width within a range of 10-1000 femtoseconds (fs).

15. The method of claim 12, wherein an energy of the laser beam is within a range of 1 micro-joule (0) to 10 milli-joules (mJ).

16. The vitrectomy probe of claim 12, wherein mechanically agitating the optical fiber causes the laser beam to move back and forth in a linear pattern across the port such that, when at one end of the pattern, the laser beam is projected across the first side of the port, and wherein the laser beam, when at an opposing end of the pattern, is projected across the second side of the port.

17. The vitrectomy probe of claim 16, wherein a laser beam path traverses the port from the first side of the port to the second side of the port to cover a port opening on both sides of the longitudinal axis such that the vitreous humor entering the port opening is severed by the scanning laser beam.

18. The vitrectomy probe of claim 12, wherein mechanically agitating the optical fiber causes the laser beam to move in a random pattern between the first side and the second side of the port.

19. The vitrectomy probe of claim 4, wherein a width of the laser beam is substantially smaller than the width of the port and wherein scanning the laser beam between the first side and the second side of the port allows the laser beam to traverse the width of the port to sever the vitreous humor entering the port.

20. The vitrectomy probe of claim 9, wherein a width of the laser beam is substantially smaller than the width of the port and wherein scanning the laser beam between the first side and the second side of the port allows the laser beam to traverse the width of the port to sever the vitreous humor entering the port.

* * * * *